(12) United States Patent
Sabate et al.

(10) Patent No.: US 10,746,084 B2
(45) Date of Patent: Aug. 18, 2020

(54) LIQUID DRIVEN THERMAL MODULE AND THERMAL MANAGEMENT SYSTEM

(71) Applicant: General Electric Company, Schenectady, NY (US)

(72) Inventors: Juan Antonio Sabate, Gansevoort, NY (US); Ruxi Wang, Cohoes, NY (US); Karthik Kumar Bodla, Watervliet, NY (US); Krishna Mainali, Niskayuna, NY (US); Yash Veer Singh, Niskayuna, NY (US); Gary Dwayne Mandrusiak, San Diego, CA (US); William John Bonneau, Wauwatosa, WI (US); Douglas Carl Hofer, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/218,477

(22) Filed: Dec. 13, 2018

(65) Prior Publication Data
US 2020/0191042 A1    Jun. 18, 2020

(51) Int. Cl.
*F01P 7/04* (2006.01)
*A61B 6/00* (2006.01)

(52) U.S. Cl.
CPC .......... *F01P 7/044* (2013.01); *A61B 6/4488* (2013.01)

(58) Field of Classification Search
CPC combination set(s) only.
See application file for complete search history.

(56) References Cited

U.S. PATENT DOCUMENTS

| 1,372,768 A | * | 3/1921 | Mott | .................... G01F 11/10 |
| | | | | 222/56 |
| 1,484,934 A | * | 2/1924 | Dalrymple | ............. F23N 1/06 |
| | | | | 110/348 |

(Continued)

OTHER PUBLICATIONS

Concentric, Hydraulic Fan Drive Systems, Concentric AB-Fan Drive-US-2011-6, pp. 1-24.

(Continued)

*Primary Examiner* — Binh B Tran
*Assistant Examiner* — Krystal Robinson
(74) *Attorney, Agent, or Firm* — Andrus Intellectual Property Law, LLP

(57) ABSTRACT

At least one thermal module in fluidic communication with the one or more electronic components. The thermal module including a hydraulic motor operable to rotate a motor output shaft. The module further including a fan coupled to the motor output shaft, at least one heat exchanger in fluidic communication with the fan to provide passage therethrough of an air stream in response to rotational movement of the fan, and a conduit carrying a pressurized liquid stream through the hydraulic motor and each of the at least one heat exchanger. The pressurized liquid stream causing the motor output shaft to rotate and wherein heat in one of the air stream or the pressurized liquid stream is passed through each of the at least one heat exchanger and rejected into the other of the air stream or the pressurized liquid stream. A thermal management system including the at least one thermal module is disclosed.

22 Claims, 6 Drawing Sheets

(56) References Cited

U.S. PATENT DOCUMENTS

| | | | | |
|---|---|---|---|---|
| 1,973,291 A * | 9/1934 | Moore | F25D 31/006 | 165/73 |
| 2,123,816 A * | 7/1938 | Utsman | F24F 6/06 | 261/30 |
| 2,592,612 A * | 4/1952 | Smith, Jr. | F23D 11/08 | 417/316 |
| 2,594,460 A * | 4/1952 | Lauck | F01P 7/044 | 236/35 |
| 3,226,602 A * | 12/1965 | Elfving | F28D 15/0233 | 361/700 |
| 3,942,486 A * | 3/1976 | Kirchner | F01P 7/044 | 123/41.12 |
| 4,062,329 A * | 12/1977 | Rio | F01P 7/044 | 123/41.12 |
| 4,320,431 A * | 3/1982 | Bell | F16C 17/246 | 361/23 |
| 5,050,037 A * | 9/1991 | Yamamoto | H01L 23/4735 | 361/699 |
| 5,063,475 A * | 11/1991 | Balan | G06F 1/20 | 165/80.3 |
| 5,165,377 A | 11/1992 | Hosseini | | |
| 5,190,099 A * | 3/1993 | Mon | H01L 23/467 | 165/104.33 |
| 5,285,347 A * | 2/1994 | Fox | G06F 1/20 | 165/80.3 |
| 5,390,734 A * | 2/1995 | Voorhes | F28F 13/00 | 165/185 |
| 5,473,508 A * | 12/1995 | Porter | H01L 23/467 | 165/80.3 |
| 5,531,190 A | 7/1996 | Mork | | |
| 5,546,272 A * | 8/1996 | Moss | G06F 1/20 | 361/679.48 |
| 5,831,824 A * | 11/1998 | McDunn | H05K 7/20345 | 361/699 |
| 6,263,957 B1 * | 7/2001 | Chen | H01L 23/473 | 165/104.33 |
| 6,351,381 B1 * | 2/2002 | Bilski | F28D 15/0266 | 165/104.33 |
| 6,381,130 B1 * | 4/2002 | Yen | G11B 33/126 | 361/679.33 |
| 6,462,949 B1 * | 10/2002 | Parish, IV | F28D 15/0266 | 165/80.4 |
| 6,536,516 B2 * | 3/2003 | Davies | F02M 31/20 | 165/170 |
| 6,600,649 B1 * | 7/2003 | Tsai | H01L 23/473 | 165/104.33 |
| 6,749,012 B2 * | 6/2004 | Gwin | F28F 9/002 | 165/104.33 |
| 6,763,880 B1 * | 7/2004 | Shih | G06F 1/20 | 165/104.22 |
| 6,827,131 B1 * | 12/2004 | Chang | F28D 1/024 | 165/121 |
| 7,009,842 B2 * | 3/2006 | Tilton | H01L 23/4735 | 165/80.4 |
| 7,215,546 B2 * | 5/2007 | Hata | F04D 29/588 | 165/104.33 |
| 7,251,137 B2 * | 7/2007 | Iijima | F04D 13/0673 | 165/104.33 |
| 7,273,088 B2 * | 9/2007 | Malone | G06F 1/20 | 165/104.33 |
| 7,280,358 B2 * | 10/2007 | Malone | G06F 1/20 | 165/104.33 |
| 7,367,384 B2 * | 5/2008 | Madara | G06F 1/203 | 165/122 |
| 7,371,056 B2 * | 5/2008 | Ito | F04D 13/0673 | 361/695 |
| 7,467,657 B2 | 12/2008 | Pawiak, III et al. | | |
| 7,486,513 B2 * | 2/2009 | Hall | G06F 1/20 | 165/104.33 |
| 7,489,057 B2 * | 2/2009 | Zhou | H02K 9/19 | 310/61 |
| 7,508,672 B2 * | 3/2009 | Hamman | F28D 15/00 | 165/104.33 |
| 7,509,999 B2 * | 3/2009 | Angelis | F04D 13/12 | 165/247 |
| 7,652,884 B2 * | 1/2010 | Suzuki | G06F 1/203 | 165/80.4 |
| 7,701,715 B2 * | 4/2010 | Suzuki | G06F 1/203 | 165/80.4 |
| 7,957,132 B2 * | 6/2011 | Fried | F28D 15/0266 | 361/679.47 |
| 7,978,472 B2 * | 7/2011 | Campbell | H05K 7/20781 | 361/699 |
| 8,196,610 B2 * | 6/2012 | Murakami | F25B 41/04 | 138/45 |
| 8,422,218 B2 * | 4/2013 | Fried | F28D 15/0266 | 361/679.47 |
| 8,514,575 B2 * | 8/2013 | Goth | H05K 7/20781 | 361/691 |
| 8,699,660 B2 | 4/2014 | Joshi et al. | | |
| 8,850,816 B2 * | 10/2014 | North | F01K 11/02 | 60/618 |
| 9,089,078 B2 * | 7/2015 | Branton | H05K 7/20263 | |
| 9,140,475 B2 * | 9/2015 | Schrader | F25B 49/02 | |
| 9,257,883 B2 * | 2/2016 | Buttner | H02K 1/32 | |
| 9,538,688 B2 * | 1/2017 | Fricker | H05K 7/20809 | |
| 10,071,270 B2 * | 9/2018 | Krekoukis | A01M 7/0014 | |
| 10,448,543 B2 * | 10/2019 | Farshchian | H05K 7/2029 | |
| 2003/0209343 A1 * | 11/2003 | Bingler | F04D 29/582 | 165/80.4 |
| 2003/0214786 A1 * | 11/2003 | Niwatsukino | H01L 23/473 | 361/699 |
| 2004/0042176 A1 * | 3/2004 | Niwatsukino | F28D 15/0266 | 361/699 |
| 2004/0050533 A1 * | 3/2004 | Chesser | G06F 1/20 | 165/46 |
| 2005/0180105 A1 * | 8/2005 | Matsushima | G06F 1/206 | 361/699 |
| 2005/0230083 A1 * | 10/2005 | Hsieh | G06F 1/20 | 165/80.4 |
| 2006/0032625 A1 * | 2/2006 | Angelis | F04D 25/0613 | 165/247 |
| 2006/0045734 A1 * | 3/2006 | Hong | F04D 13/0673 | 415/206 |
| 2006/0283579 A1 * | 12/2006 | Ghosh | H01L 23/473 | 165/104.33 |
| 2007/0097637 A1 * | 5/2007 | Chen | F28D 15/0266 | 361/696 |
| 2007/0175610 A1 * | 8/2007 | Yeh | H01L 23/473 | 165/80.4 |
| 2008/0043433 A1 * | 2/2008 | Joshi | H01L 23/467 | 361/696 |
| 2008/0070492 A1 * | 3/2008 | Koch | H05K 7/20754 | 454/184 |
| 2008/0151496 A1 * | 6/2008 | Lai | H05K 7/20572 | 361/695 |
| 2008/0173427 A1 * | 7/2008 | Schumacher | H05K 7/20609 | 165/104.14 |
| 2009/0084112 A1 * | 4/2009 | Ham | F02B 29/0481 | 62/3.2 |
| 2009/0097202 A1 * | 4/2009 | Gipson | B01D 46/0067 | 361/695 |
| 2009/0129020 A1 * | 5/2009 | Fujiwara | G06F 1/203 | 361/697 |
| 2009/0160443 A1 | 6/2009 | Albrecht | | |
| 2009/0161312 A1 * | 6/2009 | Spearing | H05K 7/20772 | 361/679.47 |
| 2009/0180253 A1 * | 7/2009 | Chang | G06F 1/203 | 361/695 |
| 2010/0157522 A1 * | 6/2010 | Refai-Ahmed | G06F 1/20 | 361/679.54 |
| 2013/0044430 A1 * | 2/2013 | Carl, Jr. | H05K 7/20772 | 361/695 |
| 2015/0160702 A1 * | 6/2015 | Franz | G06F 1/20 | 361/679.47 |
| 2016/0353604 A1 * | 12/2016 | Lavie | H05K 7/20572 | |
| 2019/0338783 A1 * | 11/2019 | Fan | H05K 7/20272 | |

(56) References Cited

U.S. PATENT DOCUMENTS

OTHER PUBLICATIONS

PCT application PCT/US2019/066228 filed Dec. 13, 2019, International Search Report/Written Opinion dated Apr. 1, 2020, 13 pages.

* cited by examiner

LIQUID DRIVEN THERMAL MODULE AND THERMAL MANAGEMENT SYSTEM

BACKGROUND

The subject matter described herein relates generally to thermal management of electronic components, and more particularly, to a thermal module and implementation in a thermal management system for cooling and/or heating hot electronic components, such as electronic components of magnetic resonance imaging (MRI) system.

MRI systems may include electronic components, such as low noise amplifiers, complex digital signal image processors and high-power RF amplifiers. There is a present desire to place all of the electronic components used in an MRI system inside the scan room next to the MRI machine. In operation, the electronic components may generate a considerable amount of heat which may affect the operation of the MRI system. For example, the electronic components generate waste heat that must be continually addressed so that the components do not overheat. The heat may cause damage to the electronics, and if vented to the scan room it will heat up the room, which will require an HVAC system to avoid exceeding the environment specs for patient comfort.

At least some known MRI systems include a cooling system that utilizes the placement of fans or the like, proximate the MRI system, and more particularly in the scan room. The use of electric fans or fan motors inside the scan room may affect not only the magnetic fields of the MRI scanner in way that compromises image quality, but may also make servicing and/or repair of the MRI scanner difficult and/or dangerous. In addition, it is desired to have all electronics contained in a sealed enclosure, such as a cabinet, to minimize the risk of electromagnetic interference (EMI) from the electronics, further compromising image quality. With a sealed enclosure, the heat generated by the electronics housed therein, has no place to go, thus the temperatures within the cabinet increase over time. This presents challenges from a thermal management perspective.

Accordingly, there is a need for a thermal management system and method for heating and/or cooling electronic components that allows positioning proximate the electronics sought to be thermally managed. Further there is a need for a thermal management system that provides cooling of electronic components of an MRI system while minimizing the risk of EMI from the electronics, so as to not compromise image quality.

BRIEF DESCRIPTION

In one aspect, a thermal module is provided. The thermal module includes a hydraulic motor, a fan, and at least one heat exchanger and a conduit. The hydraulic motor is operable to rotate a motor output shaft. The fan is coupled to the motor output shaft. The at least one heat exchanger is in fluidic communication with the fan to provide passage therethrough of an air stream in response to rotational movement of the fan. The conduit carries a pressurized liquid stream through the hydraulic motor and the at least one heat exchanger. The pressurized liquid stream causes the motor output shaft to rotate. The heat in one of the air stream or the pressurized liquid stream is passed through each of the at least one heat exchanger and rejected into the other of the air stream or the pressurized liquid stream.

In another aspect, a thermal management system is provided. The thermal management system includes an outer enclosure, an electronic component enclosure disposed in the outer enclosure, one or more electronic components disposed in the electronic component enclosure and at least one thermal module disposed in the outer enclosure and in fluidic communication with the one or more electronic components. The thermal module includes a hydraulic motor, a fan, at least one heat exchanger, and a conduit. The hydraulic motor is operable to rotate a motor output shaft. The fan is coupled to the motor output shaft. The at least one heat exchanger is in fluidic communication with the fan to provide passage therethrough of an air stream in response to rotational movement of the fan. The conduit carries a pressurized liquid stream through the hydraulic motor and the at least one exchanger. The pressurized liquid stream causes the motor output shaft to rotate. One of heat in the air stream passing through the each of the at least one heat exchanger is rejected into the pressurized liquid stream or heat in the pressurized liquid stream passing through the conduit is rejected into the air stream passing through each of the at least one heat exchanger.

In yet another aspect, a thermal management system is provided. The thermal management system includes an outer enclosure, one or more electronic component enclosure disposed in the outer enclosure, one or more electronic components disposed in the electronic component enclosure and at least one thermal module disposed in each of the at least one outer enclosure and in fluidic communication with the at least one electronic component. The thermal module includes a hydraulic motor that is operable to rotate a motor output shaft, a fan coupled to the motor output shaft, at least one heat exchanger in fluidic communication with the fan to provide passage therethrough of an air stream in response to rotational movement of the fan and a conduit carrying a pressurized liquid stream through the hydraulic motor and the at least one heat exchanger. The pressurized liquid stream causes the motor output shaft to rotate. Heat in the air stream passing through each of the at least one heat exchanger is rejected into the pressurized liquid stream.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present disclosure, including the best mode thereof to one skilled in the art, is set forth more particularly in the remainder of the specification, including reference to the accompanying figures, in which.

Corresponding reference characters indicate corresponding parts throughout the several views of the drawings.

DETAILED DESCRIPTION OF THE DISCLOSURE

Figure 1:
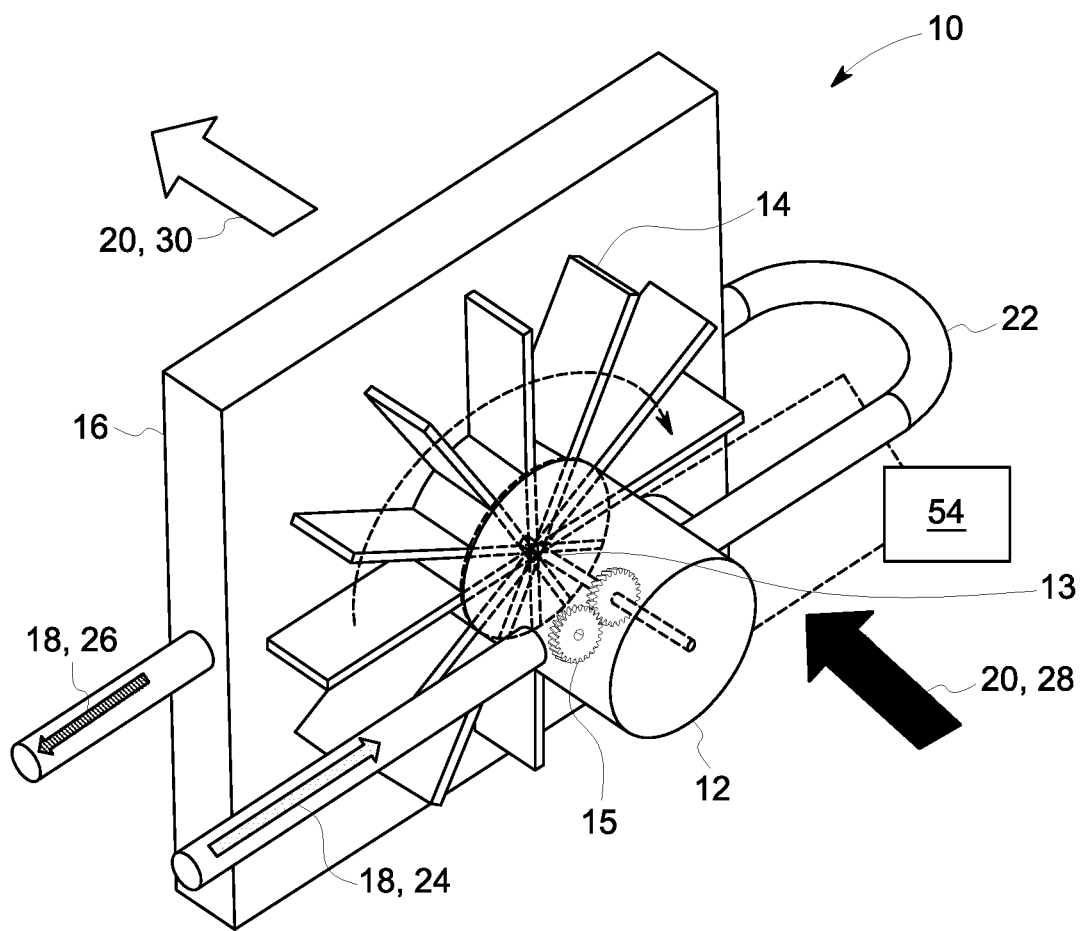
FIG. 1 is a schematic view of an embodiment of a thermal module including a liquid stream driven fan and heat exchanger, in accordance with one or more embodiments of the present disclosure.

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Embodiments of the present disclosure provide for a thermal management system to heat and/or cool electronic components. In particular, embodiments of the present disclosure provide for a thermal management system to cool electronic components, such as those used in an MRI system. The thermal management system comprises a fan and heat exchanger module that is driven by a liquid, and more specifically, a hydraulic fluid, which can be the cooling fluid in the system. As a result, the disclosed fan and heat exchanger module provides for the heating and/or cooling of electronics disposed within a sealed enclosure. In an embodiment, the disclosed fan and heat exchanger module provides for the cooling of electronics in close proximity to a MRI scanner, while minimizing the risk of electromagnetic interference (EMI) from the electronics.

Each example is provided by way of explanation of the disclosure, not limitation of the disclosure. In fact, it will be apparent to those skilled in the art that modifications and variations can be made in the present disclosure without departing from the scope or spirit thereof. For instance, features illustrated or described as part of one embodiment may be used on another embodiment to yield a still further embodiment. Thus, it is intended that the present disclosure covers such modifications and variations as come within the scope of the appended claims and their equivalents. Although exemplary embodiments of the present disclosure will be described generally in the context of a MRI system, for purposes of illustration, one of ordinary skill in the art will readily appreciate that embodiments of the present disclosure may be used in combination with any electronic components for heating and/or cooling, such as those associated with CT scanners, computers, or the like, and is not intended to be limiting to a cooling implementation with MRI system electronic components.

Thermal management systems, employing heat exchangers, are widely used in applications such as space heating, refrigeration, air conditioning, power plants, chemical processing plants and numerous engines, machines, vehicles and electrical devices. Heat exchangers may be employed in these various applications for efficient heat transfer from one medium to another, and more particularly to exchange heat between two fluids. For example, a first fluid at a higher temperature may be passed through one or more first channels or passageways, while a second fluid at a lower temperature may be passed through one or more second channels or passageways. The first and second passageways may be in contact or close proximity, allowing heat from the first fluid to be passed to the second fluid. Thus, the temperature of the first fluid may be decreased and the temperature of the second fluid may be increased.

In general, heat exchangers may be classified according to their flow configuration as crossflow heat exchanging systems, parallel heat exchanging systems, counter flow heat exchanging systems, or in terms of their geometry and design as shell and tube heat exchangers, plate heat exchangers, and finned tube heat exchangers, among many others.

Referring now to the drawings, wherein identical numerals indicate the same elements throughout the figures, FIG. 1 provides a schematic view of an exemplary thermal module 10, for use in a thermal management system, described herein. In the exemplary embodiment, the thermal module 10 comprises a hydraulic motor 12 for driving a fan 14 and a heat exchanger 16. The thermal module 10 is in fluid communication with a liquid stream 18 and an air stream 20. A hydraulic fluid conduit 22 provides for the flow therethrough of the liquid stream 18.

As previously alluded to, in the illustrated embodiment, the hydraulic motor 12 is liquid driven, rotating a motor output shaft 13 by passing the liquid stream 18 through the hydraulic motor 12. In the illustrated embodiment, the hydraulic motor 12 includes an internal gear set 15. In an alternate embodiment, the hydraulic motor 12 in lieu of a gear set, may include any means for operably rotating the motor output shaft 13 in response to the flow of the liquid stream 18. In the illustrated embodiment, the liquid stream 18 is in direct contact with the internal gear set 15 of the hydraulic motor 12 and at a sufficient pressure to provide rotating of the motor output shaft 13, which in turn provides for rotating of the fan 14, as indicated by directional arrow. The fan 14 is one of a puller-type or pusher-type fan (described presently) dependent upon the desired flow stream within the thermal management system. During operation, the gear set 15 converts the hydraulic pressure and flow of the liquid stream 18 into torque and angular displacement (rotary mechanical power) that is applied to the fan 14 via the shaft 13. During operation, the liquid stream 18 is moved into the hydraulic motor 12 causing the matched gear set 15 to rotate. As illustrated, one of the gears 15 is connected to the motor output shaft 13, producing the rotary mechanical power. In an embodiment, a speed control mechanism 17, such as a gear box, a belt and pulley system, or the like, may be coupled to the hydraulic motor 12 and the fan 14 and configured to control the speed of the hydraulic motor 12 and the fan 14 and provide for optimization independent of one another.

As previously indicated, the thermal module 10 employs the heat exchanger 16 for efficient heat transfer from one medium to another, and more particularly to exchange heat between the two fluids, the liquid stream 18 and the air stream 20. In this particular embodiment, the heat exchanger 16 is a cross-flow heat exchanging system. The hydraulic fluid conduit 22, passes through the heat exchanger 16, and is configured having a generally tubular structure and may be referred to herein as a heat exchanging tube. The heat exchanger 16 may optionally employ fins to provide an increase in a surface area of the conduit 22. In alternate embodiments, the hydraulic fluid conduit 22 may include other structural geometries. The hydraulic fluid conduit 22 defines a fluid flow path in a direction, as indicated by directional arrows, for the liquid stream 18.

The heat exchanging system, and more particularly, the heat exchanger 16 removes heat from one of the liquid stream 18 or the air stream 20 via a process of heat transfer. The heat transfer is a physical phenomenon that facilitates heat exchange between fluids at different temperatures through a conducting wall. In one embodiment, the heat exchanging system works on the phenomena of heat transfer to cool the air stream 20. Heat is removed from the air stream 20 by the cooler liquid stream 18. The liquid stream 18 exits the heat exchanger 16, and more particularly, the thermal module 10 and is cooled via a heat sink (not shown), or the like, prior to reentering the thermal module as a cooled liquid stream 18. In an alternate embodiment, when the thermal management system is operated in reverse, the heat exchanging system works on the phenomena of heat transfer to cool the liquid stream 18.

In an exemplary embodiment, during operation, the thermal module 10 is configured to allow the inlet air stream 20, at a higher temperature, to pass through the heat exchanger 16, while the inlet liquid stream 18 is at a lower temperature and passes through the hydraulic fluid conduit 22. The air stream 20 is in contact with the hydraulic fluid conduit 22, allowing heat from the air stream 20 to be passed to the liquid stream 18. In the illustrated embodiment, the liquid stream 18 enters the thermal module 10 as a cold fluid, and more particularly as a first temperature liquid stream 24 and exits the module 10 as a hot fluid, and more particularly at a second temperature liquid stream 26, wherein the second temperature is greater than the first temperature. The air stream 20 enters the heat exchanger 16 as a hot fluid, and more particularly at a first temperature air fluid flow 28 and exits the heat exchanger as a cool fluid, and more particularly at a second temperature air fluid flow 30, wherein the second temperature is less than the first temperature. Thus, the temperature of the air stream 20 is decreased upon exiting the heat exchanger 16 and the temperature of the liquid stream 18 is increased upon passing through the heat exchanger 16. As previously described, in an alternate embodiment, the thermal module 10 may be operated in reverse, providing the heat exchanging system, and more particularly, a cool air stream to cool a hot liquid stream.

Figure 2:
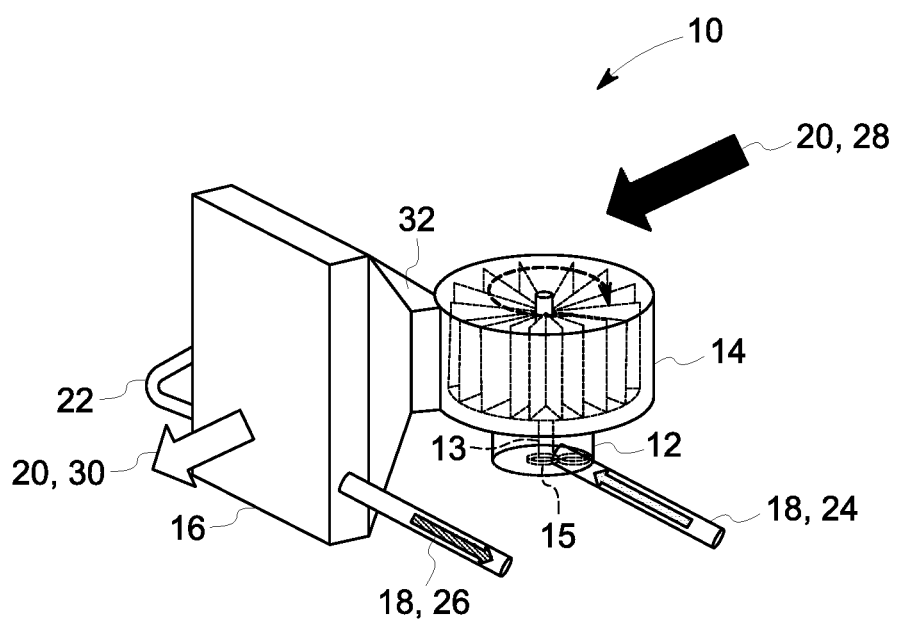
FIG. 2 is a schematic view of another embodiment of a thermal module including a liquid stream driven fan and heat exchanger, in accordance with one or more embodiments of the present disclosure.

Referring now to FIG. 2, illustrated is an alternate configuration for the thermal module 10, whereby the hydraulic motor 12, the fan 14 and the heat exchanger 16 are not oriented in a linear manner, and may employ ducting 32 to achieve a non-linear configuration. The thermal module 10 of FIG. 2, operates in generally the same manner as the previously described embodiment, or in reverse. More particularly, in the exemplary embodiment the thermal module 10 is configured to provide the inlet air stream 20, at a higher temperature, to pass through the heat exchanger 16, while the inlet liquid stream 18 is at a lower temperature and passes through the hydraulic fluid conduit 22. The air stream 20 is in contact with the hydraulic fluid conduit 22, allowing heat from the air stream 20 to be passed to the liquid stream 18. Simultaneous therewith, the inlet liquid stream 18 provides spinning of the motor output shaft 13 in the hydraulic motor 12, which in turn provides for spinning of the fan 14, as indicated by directional arrow.

Referring now to FIGS. 3-6, illustrated are a plurality of embodiments illustrating varying configurations for a thermal management, including the thermal module 10 of FIG. 1. It is noted in the drawings, for ease in determining air flow patterns in the thermal management system, that the first temperature air fluid flow 28 is indicated as a dark solid arrow and the second temperature air fluid flow 30, is indicated as a light solid arrow. It should again be noted, that a thermal management system that operates in reverse so as to provide heating of the electronic components is encompassed herein.

As illustrated in FIGS. 3-6, the thermal module 10 is housed within an enclosure (described presently) that additionally houses one or more electronic components (described presently) for cooling. As the thermal management system is configured as a closed system, with air being recirculated by the thermal module 10 and the liquid stream 18 providing both a driving force to the fan 14 and absorbing heat from the air stream 20 in the heat exchanger 16, there is no need for air inlets and outlets, thus providing better protection to the electronics housed therein from dust and/or humidity. The only required openings (described presently) in the thermal management system, and more specifically, the enclosure, are for the hydraulic fluid conduit 22 carrying the liquid stream 18 externally for cooling. Additionally, no heat is rejected outside the thermal management system, thereby the burden on an external cooling system (e.g., HVAC in a MRI scan room) is eliminated.

Figure 3:
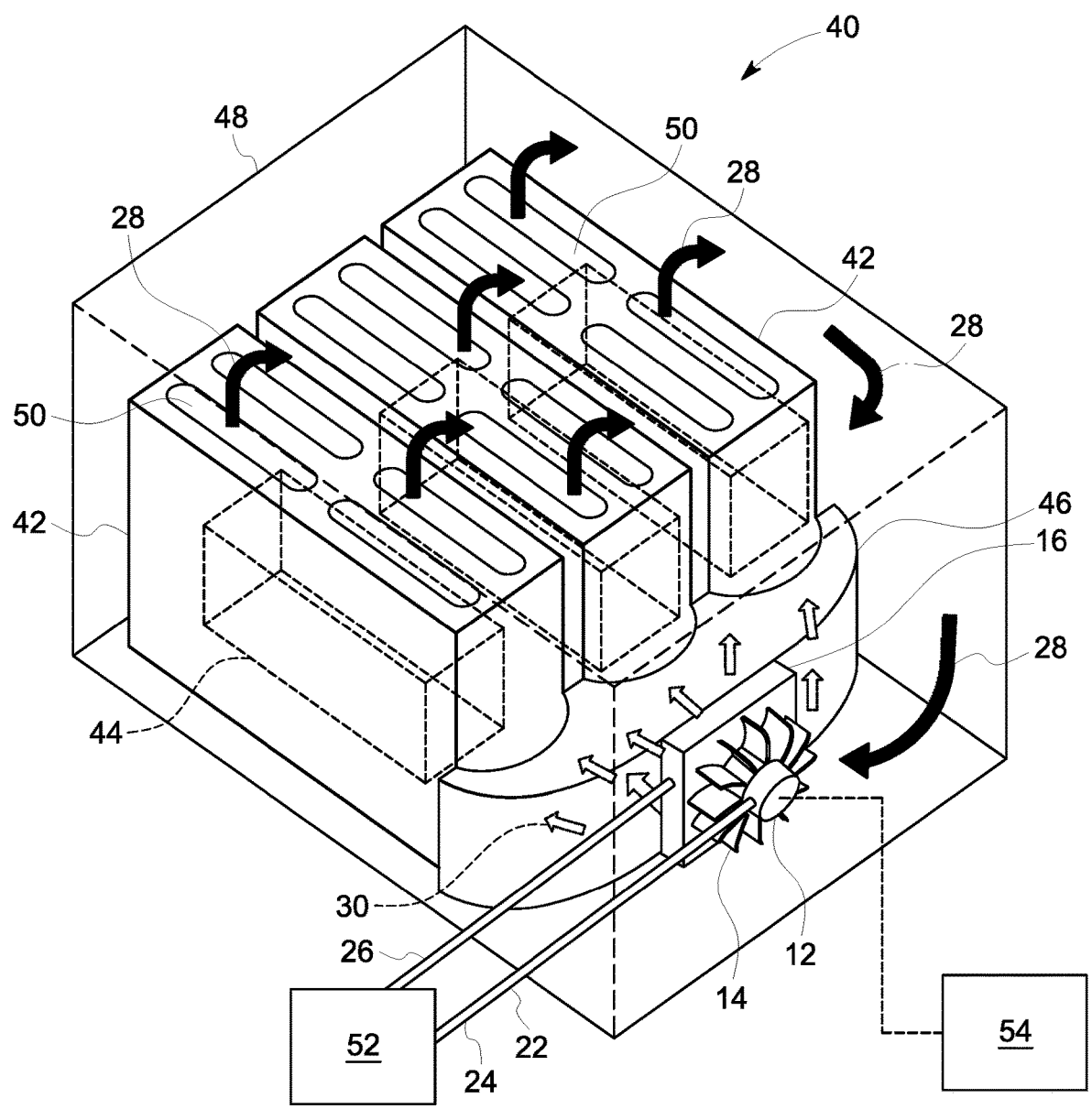
FIG. 3 is a schematic view of a thermal management system, including the thermal module of FIG. 1, and indicating a typical flow of air therethrough, in accordance with one or more embodiments of the present disclosure.

Referring more specifically to FIG. 3, illustrated is a thermal management system, generally referenced 40, including the thermal module 10 of FIG. 1. The thermal management system 40 further includes at least one electronic component enclosure 42, having disposed therein a plurality of electronic components 44, such as amplifiers, at least one duct 46 coupling the thermal module 10 and the at least one electronic component enclosure 42, all sealingly housed within an outer enclosure 48. As illustrated, in this particular embodiment, three electronic component enclosures 42 are in fluid communication with the thermal module 10 via the duct 46. A single thermal module 10 is utilized for cooling the plurality of electronic component enclosures 42. In an alternate embodiment, more than one thermal module 10 may be utilized to cool the plurality of electronic component enclosures 42.

As indicated by the directional arrows in FIG. 3, during operation, the electronic components 44 housed within the electronic component enclosures 42 generate heat that is output via a plurality of outlets 50 as a hot air flow, and more particularly as the first temperature air stream 28. The first temperature air stream 28 flows toward the thermal module 10 and is pushed through the heat exchanger 16 via the fan 14. In this particular embodiment, the fan 14 is a push-type fan. The fan 14 is driven by the first temperature liquid stream 24. As the first temperature air stream 28 is pushed through the heat exchanger 16, it is cooled by the coolant fluid via the conduit 22 and the first temperature liquid stream 24, resulting in the output of the second temperature liquid stream 26 from the heat exchanger 16. The cooled air flow, and more particularly the second temperature air stream 30 is directed via the duct 46 to cool the electronic components 44 disposed within the electronic component enclosures 42. In addition, the hot second temperature liquid stream 26 flows via the conduit 22 to an exterior of the outer enclosure 48 where it is cooled via a heat sink 52, or the like, and recirculated back into the interior of the outer enclosure 46 as the first temperature liquid stream 24.

The thermal management system 40 as disclosed allows for the use of an existing hydraulic coolant line that may be present within an MRI scan room to provide the liquid stream 18 in the conduit 22. Controlling the thermal management system 40 is simplified as only the flow, pressure and temperature of the liquid stream 18 needs to be monitored for regulating the cooling. A feedback controller 54, may be used to adjust the flow/pressure to maintain the internal temperature of the electronic component enclosures 42.

In an alternate embodiment, as previously mentioned, the thermal management system 40 may be operated in reverse to provide heating, and more specifically, a heated air stream to the electronic components 44 within each of the electronic component enclosures 42.

Figure 4:
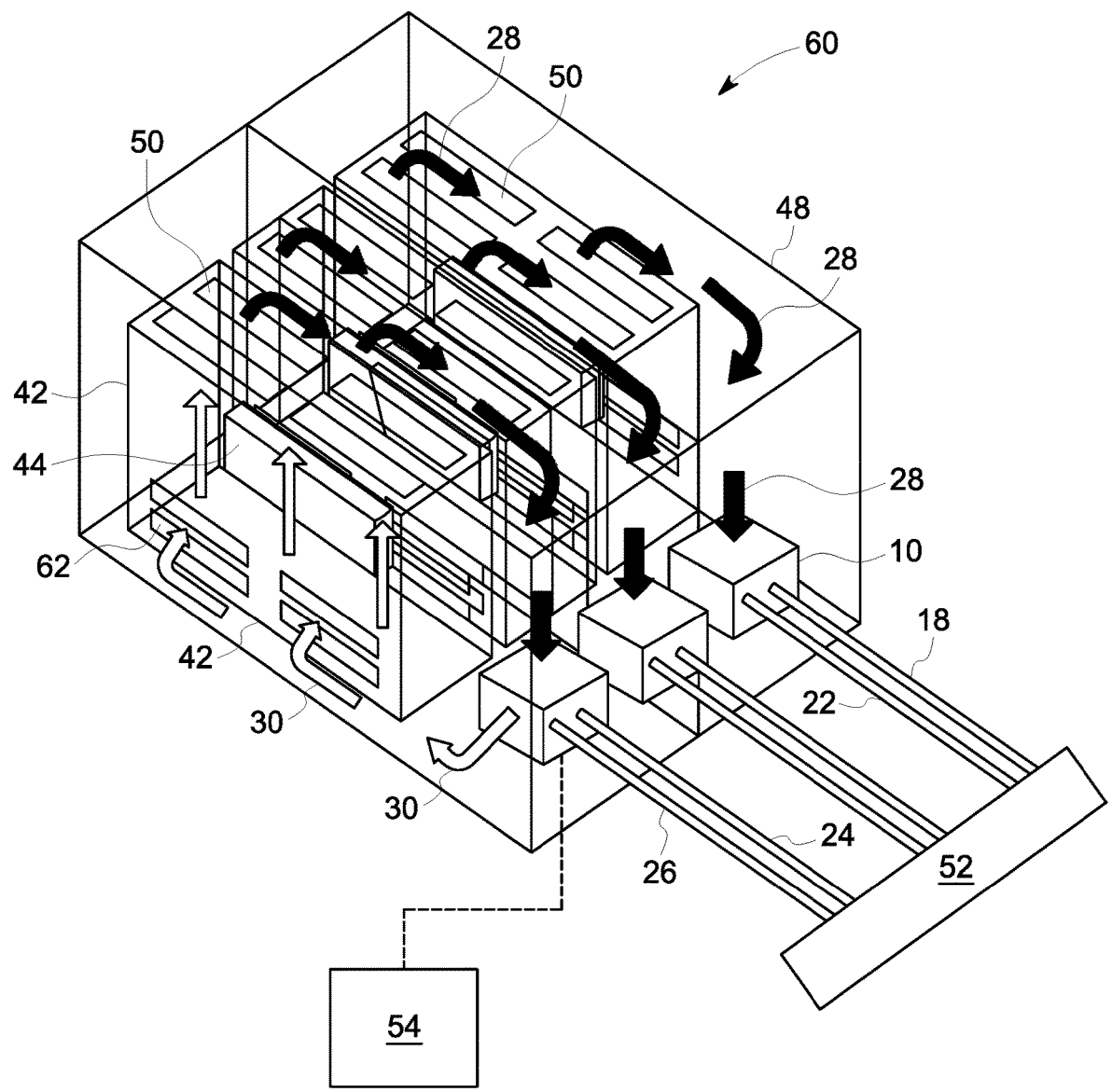
FIG. 4 is a schematic view of another embodiment of a thermal management system, including the thermal module of FIG. 2, and indicating a typical flow of air therethrough, in accordance with one or more embodiments of the present disclosure.

Referring now to FIG. 4, illustrated is a thermal management system, generally referenced 60, including the thermal module 10 of FIG. 1. The thermal management system 60 further includes at least one electronic component enclosure 42, having disposed therein a plurality of electronic components 44. The thermal module 10 and the at least one electronic component enclosure 42 are sealingly housed within an outer enclosure 48. In this particular embodiment, the thermal module 10 is positioned within the outer enclosure 48, and relative to the at least one electronic component enclosure 42 such that no ducting is required. As illustrated, in this particular embodiment, a plurality of thermal modules 10 are utilized for cooling the plurality of electronic component enclosures 42. In an alternate embodiment, a single thermal module 10 may be utilized to cool the plurality of electronic component enclosures 42.

As indicated by the directional arrows in FIG. 4, during operation, the electronic components 44 housed within the at least one electronic component enclosure 42 generate heat that is output via a plurality of outlets 50 as a hot air flow, and more particularly as the first temperature air stream 28. The first temperature air stream 28 flows toward the plurality of thermal modules 10 and is pushed through the heat exchanger 16 of each thermal module 10 via the fan 14. The fan 14 of each thermal module 10 is driven by the first temperature liquid stream 24. As the first temperature air stream 28 is pushed through the heat exchanger 16, it is cooled by removing the heat with the coolant fluid via the conduit 22 and the first temperature liquid stream 24, resulting in the output of the second temperature liquid stream 26 from the heat exchanger 16. The cooled air stream 20, and more particularly the second temperature air stream 30 is directed toward a plurality of inlets 62 in each of the electronic component enclosures 42 to cool the electronic components 44 within each of the electronic component enclosures 42. In addition, the hot second temperature liquid stream 26 flows via the conduit 22 to an exterior of the outer enclosure 48 where it is cooled via a heat sink 52, or the like, and recirculated back into the interior of the outer enclosure 46 as the first temperature liquid stream 24.

Similar to the previous embodiment, the thermal management system 60 as disclosed allows for the use of an existing hydraulic coolant line that may be present within an MRI scan room to provide the liquid stream 18 in the conduit 22. Controlling the thermal management system 60 is simplified as only the flow, pressure and temperature of the liquid stream 18 needs to be monitored for regulating the cooling. A feedback controller 54, may be used to adjusts the flow/pressure to maintain the internal temperature of the electronic component enclosures 42.

In an alternate embodiment, as previously mentioned, the thermal management system 60 may be operated in reverse to provide heating, and more specifically, a heated air stream to the electronic components 44 within each of the electronic component enclosures 42.

Figure 5:
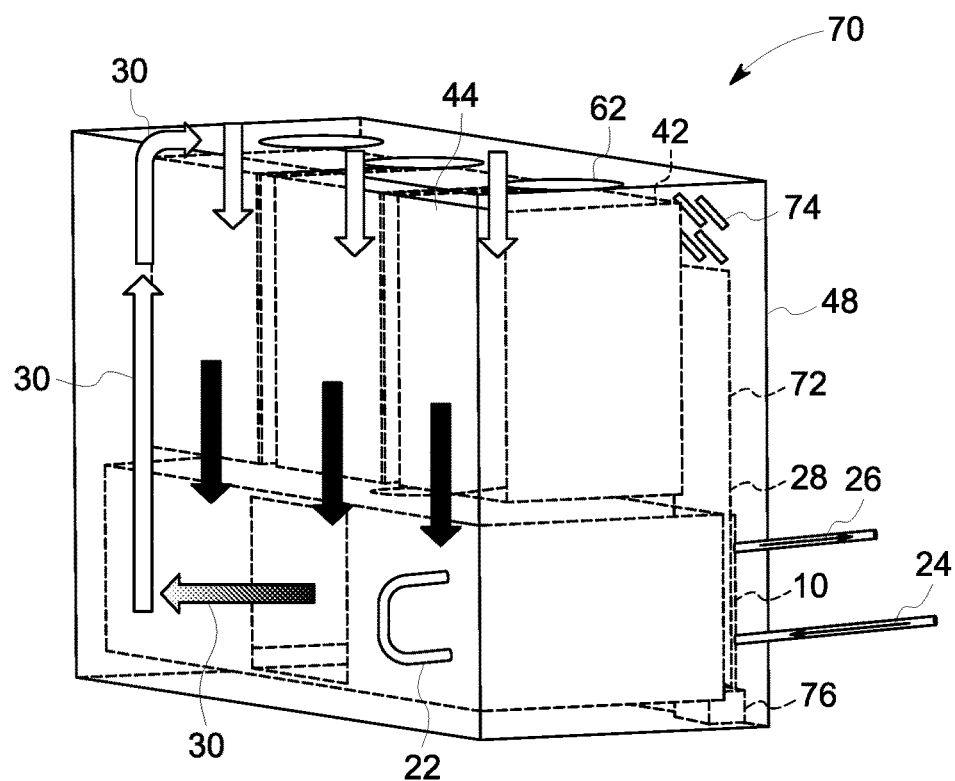
FIG. 5 is a schematic view of yet another embodiment of a thermal management system, including a thermal module, and indicating a typical flow of air therethrough, in accordance with one or more embodiments of the present disclosure.
Figure 6:
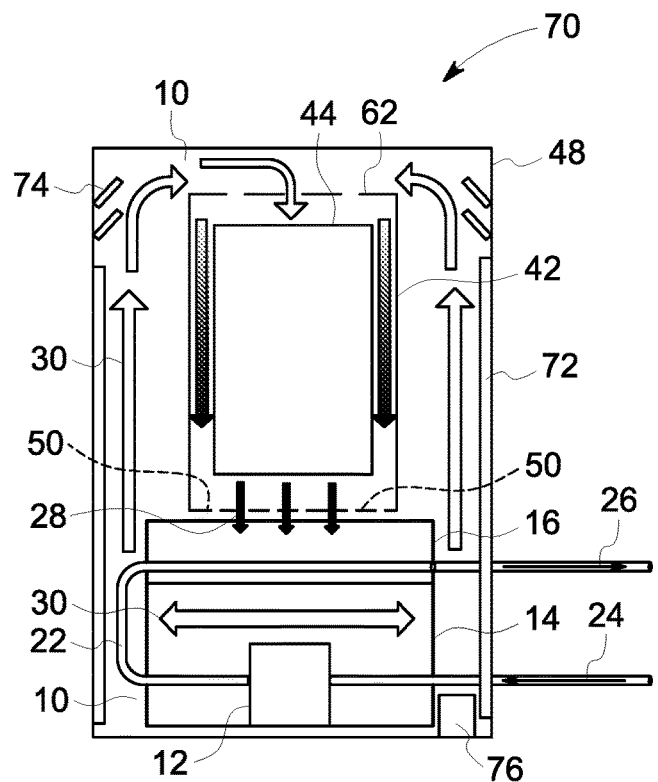
FIG. 6 is a schematic end view of the thermal management system of FIG. 5, including a thermal module, and indicating a typical flow of air therethrough, in accordance with one or more embodiments of the present disclosure.

Referring now to FIGS. 5 and 6, illustrated is another embodiment of a thermal management system, generally referenced 70, including the thermal module 10 of FIG. 1. Similar to the previously disclosed embodiments, the thermal management system 70 includes at least one electronic component enclosure 42, housing therein a plurality of electronic components 44. The thermal module 10 and the at least one electronic component enclosure 42 are sealingly housed within an outer enclosure 48. In this particular embodiment, the thermal module 10 is positioned within the outer enclosure 48 below the at least one electronic component enclosure 42. As illustrated, a single thermal module 10 is utilized for cooling the plurality of electronic component enclosures 42. In an alternate embodiment, a plurality of thermal modules 10 may be utilized to cool the plurality of electronic component enclosures 42.

As indicated by the directional arrows in FIGS. 5 and 6, during operation, the electronic components 44 housed within the electronic component enclosures 42 generate heat that is output via a plurality of outlets 50 as a hot air flow, and more particularly as the first temperature air stream 28. The first temperature air stream 28 flows toward the thermal modules 10 and, in contrast to the previous embodiments, is pulled through the heat exchanger 16 of the thermal module 10 via the fan 14, and more particularly, a pull-type fan, rather than being pushed. The fan 14 of the thermal module 10 is driven by the first temperature liquid stream 24. As the first temperature air stream 28 is pulled through the heat exchanger 16, it is cooled by removing the heat with the coolant fluid via the conduit 22 and the first temperature liquid stream 24, resulting in the output of the second temperature air stream 30 from the heat exchanger 16, and more specifically, a cooler air stream. The cooled air stream, and more particularly the second temperature air stream 30 is directed toward a plurality of inlets 62 in each of the electronic component enclosures 42 to cool the electronic components 44 within the enclosures 42. In addition, the hot second temperature liquid stream 26 flows via the conduit 22 to an exterior of the outer enclosure 48 where it is cooled via a heat sink (not shown), or the like, and recirculated back into the interior of the outer enclosure 46 as the first temperature liquid stream 24.

Similar to the previous embodiment, the thermal management system 70 as disclosed allows for the use of an existing hydraulic coolant line that may be present within an MRI scan room to provide the liquid stream 18 in the conduit 22. Controlling the thermal management system 70 is simplified as only the flow, pressure and temperature of the liquid stream 18 needs to be monitored for regulating the cooling. A feedback controller (not shown), may be used to adjust the flow/pressure to maintain the internal temperature of the electronic component enclosures 42.

In an alternate embodiment, as previously mentioned, the thermal management system 70 may be operated in reverse to provide heating, and more specifically, a heated air stream to the electronic components 44 within each of the electronic component enclosures 42.

Figure 7:
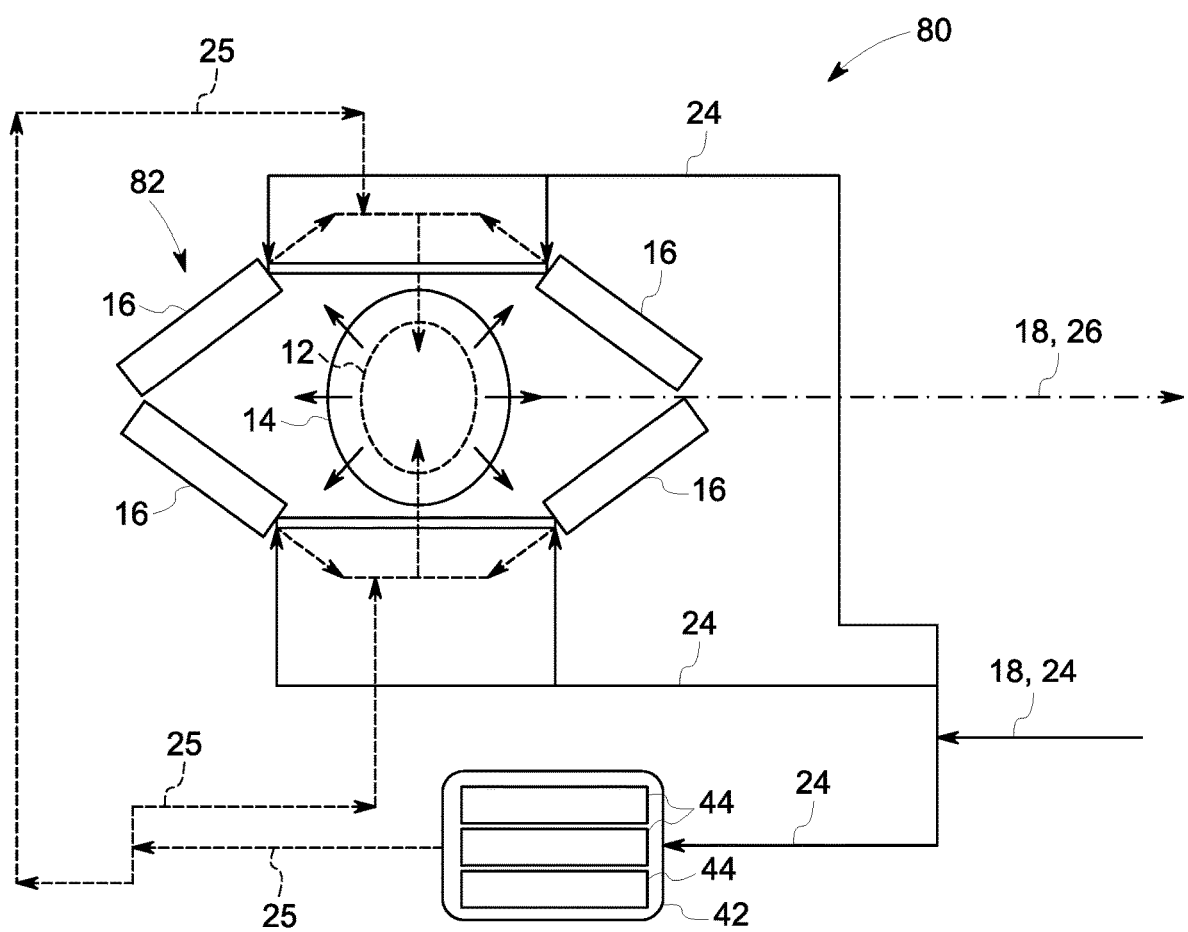
FIG. 7 is a schematic flow diagram of another embodiment of a thermal management system, including a thermal module, and indicating a typical flow of a liquid stream therethrough, in accordance with one or more embodiments of the present disclosure.
Figure 8:
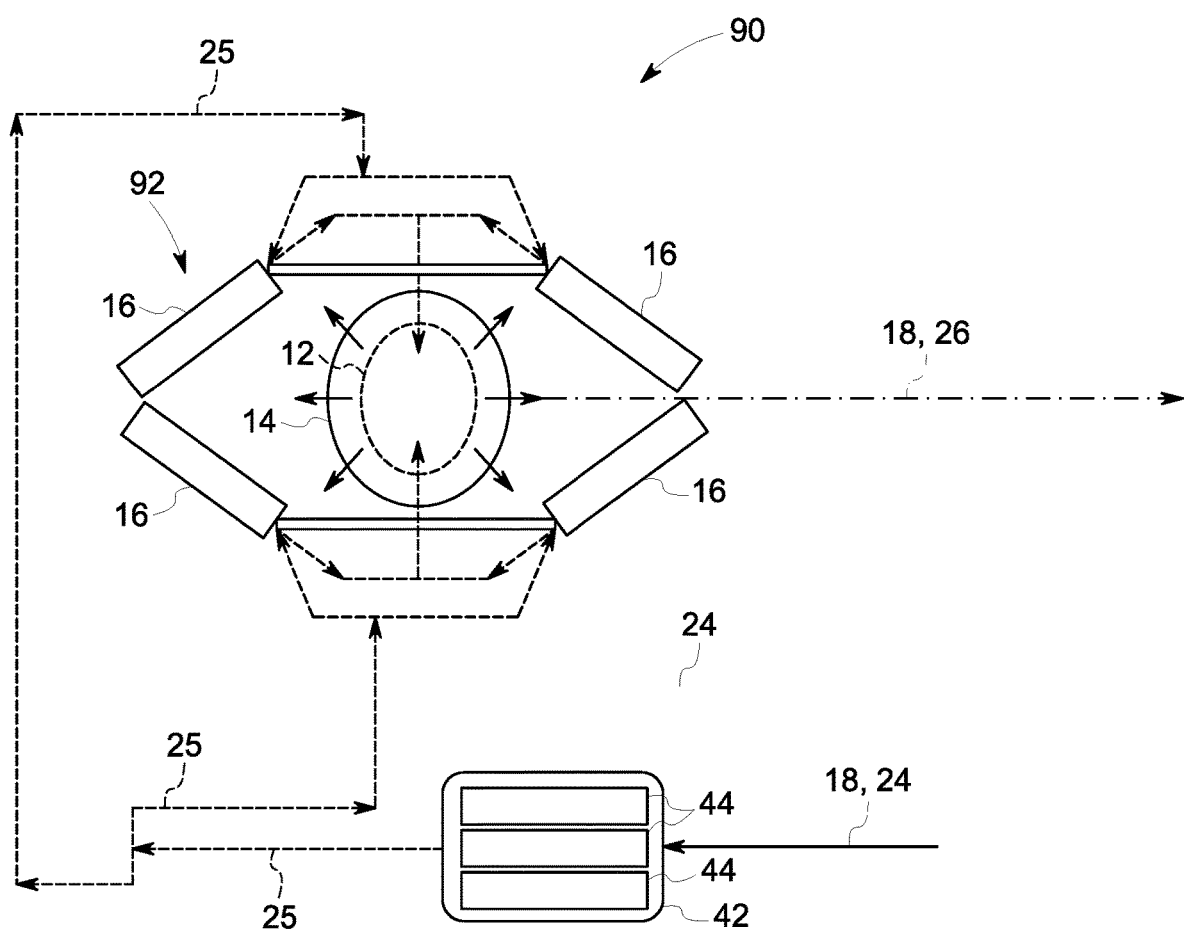
FIG. 8 is a schematic flow diagram of another embodiment of a thermal management system, including a thermal module, and indicating a typical flow of a liquid stream therethrough, in accordance with one or more embodiments of the present disclosure.

Referring now to FIGS. 7 and 8, illustrated are schematic flow diagrams of additional embodiments of the thermal management system disclosed herein. Referring more specifically to FIG. 7, illustrated is an embodiment of a thermal management system, generally referenced 80, including a thermal module 82. In this particular embodiment, the thermal module 82 includes a single hydraulic motor 12, a single fan 14, and a plurality of cross-flow heat exchangers 16 in fluid communication with the hydraulic motor 12 and fan 14. Similar to the previously disclosed embodiments, the thermal management system 80 includes at least one electronic component enclosure 42, housing therein a plurality of electronic components 44. As illustrated, a single thermal module 82 is utilized for cooling the electronic component enclosure 42. In an alternate embodiment, a plurality of thermal modules 82 may be utilized to cool one or more electronic component enclosures 42.

As previously described, during operation, the electronic components 44 housed within the electronic component enclosure 42 generate heat that is output as a hot air flow (not shown). The hot air flow (not shown) flows toward the thermal module 82 and is pushed through the heat exchangers 16 of the thermal module 82 via the fan 14, thereby cooling the air stream, as previously described. The fan 14 of the thermal module 82 is driven by a liquid stream 18. In an alternate configuration, the hot air flow (not shown) flows toward the thermal module 82 and is pulled through the heat exchangers 16 of the thermal module 82 via the fan 14, thereby cooling the hot air flow, as previously described.

As illustrated in the flow diagram of FIG. 7, in contrast to the previous embodiments, the liquid stream 18 is initially split to provide cooling to the electronic component enclosure 42, provide cooling in the heat exchangers 16 and provide an increased flow rate to the motor 12 and act as a driving force. More particularly, as illustrated, the first temperature liquid stream 24, indicated by solid directional lines, is initially split into multiple fluid flows with a portion input to the electronic component enclosure 42 and a remaining portion passing through the thermal module 82. As the first temperature liquid stream 24 passes through the electronic component enclosure 42 and provides cooling to the electronic components 44 housed therein, it is output as an intermediate temperature liquid stream 25, indicated by dashed lines, wherein the first temperature liquid stream 24 has a temperature less than a temperature of the intermediate temperature liquid stream 25. The intermediate temperature liquid stream 25 is input to the thermal module 82, mixes with the portion of the first temperature liquid stream 24 input into the motor 12 and exits the thermal module 82 as the second temperature fluid flow 26, indicated by dot-dashed lines, at a further increased temperature, having served as the cooling fluid flow in the heat exchangers 16 to cool the hot air flow (not shown). The second temperature liquid stream 26 is cooled via a heat sink (not shown), or the like, and recirculated back as the first temperature liquid stream 24.

As the first temperature air stream (not shown) passes through the heat exchangers 16, it is cooled by removing the heat with the coolant fluid flow 18, and more particularly, via a portion of the first temperature liquid stream 24 and the intermediate temperature liquid stream 25, resulting in the output of the second temperature air stream (not shown) from the heat exchangers 16, and more specifically, a cooler air stream. Similar to the previous embodiments, the cooled air stream is directed toward the electronic component enclosures 42 to cool the electronic components 44 within the enclosures 42.

Referring now to FIG. 8, illustrated is another embodiment of a thermal management system, generally referenced 90, including a thermal module 92, configured generally similar to thermal module 82 of FIG. 7, and at least one electronic component enclosure 42, housing therein a plurality of electronic components 44. As illustrated, a single thermal module 92 is utilized for cooling the electronic component enclosure 42. In an alternate embodiment, a plurality of thermal modules 92 may be utilized to cool one or more electronic component enclosures 42.

The system 90 operates similarly to the previously described embodiments, whereby the electronic components 44 housed within the electronic component enclosure 42 generate heat that is output as a hot air flow (not shown). The hot air flow (not shown) flows toward the thermal module 92 and is pushed through the heat exchangers 16 of the thermal module 92 via the fan 14, thereby cooling the hot air flow, as previously described. The fan 14 of the thermal module 92 is driven by a liquid stream 18. In an alternate configuration, the hot air flow (not shown) flows toward the thermal module 82 and is pulled through the heat exchangers 16 of the thermal module 82 via the fan 14, thereby cooling the hot air flow, as previously described.

As illustrated in the flow diagram of FIG. 8, in contrast to the embodiment of FIG. 7, the liquid stream 18 is not split and is input directly into the electronic component enclosure 42 to provide cooling to the electronic components 44. More particularly, as illustrated, the first temperature liquid stream 24, indicated by the solid directional line, is input to the electronic component enclosure 42 and passes therethrough. As the first temperature liquid stream 24 passes through the electronic component enclosure 42 and provides cooling to the electronic components 44 housed therein, it is output as an intermediate temperature liquid stream 25, indicated by dashed lines, wherein the first temperature liquid stream 24 has a temperature less than a temperature of the intermediate temperature liquid stream 25. The intermediate temperature liquid stream 25 is input to the thermal module 92, and exits the thermal module 92 as a second temperature liquid stream 26, indicated by dot-dashed line, at a further increased temperature, having served as the cooling fluid flow in the heat exchangers 16, to cool the hot air flow (not shown). The second temperature liquid stream 26 is cooled via a heat sink (not shown), or the like, and recirculated back as the first temperature liquid stream 24.

As the first temperature air stream (not shown) passes through the heat exchangers 16, it is cooled by removing the heat with the coolant fluid flow 18, and more particularly, via the intermediate temperature liquid stream 25, resulting in the output of the second temperature air stream (not shown) from the heat exchangers 16, and more specifically, a cooler air stream. Similar to the previous embodiments, the cooled air stream is directed toward the electronic component enclosures 42 to cool the electronic components 44 within the enclosures 42.

In further alternate embodiments, the liquid flow direction of FIGS. 7 and 8 may be reversed. Similar to the previous embodiments, the thermal management systems 80 and 90 provide for the use of an existing hydraulic coolant line that may be present within an MRI scan room to provide the liquid stream 18. Controlling the thermal management systems 80 and 90 is simplified as only the flow, pressure and temperature of the liquid stream 18 needs to be monitored for regulating the cooling. A feedback controller (not shown), may be used to adjust the flow/pressure to maintain the internal temperature of the electronic component enclosure 42.

In each of the disclosed embodiments, the walls of the outer enclosure 48 are not relied upon for heat rejection because all of the heat generated by the electronic components 42 is rejected to the liquid stream 18 via the heat exchanger (s) 16. Accordingly, in any of the disclosed embodiments, the thermal management system may further include sound dampeners and/or insulation 72 on the inner walls of the outer enclosure 48, as best illustrated in FIG. 6 for minimizing noise. Similarly, mechanical protection may be added to the outer enclosure 48 without a negative impact on heat rejection. Further, internal baffling, such as flow guides 74 of FIG. 6 can be implemented for better directing the air stream 18, and more particularly, the second temperature air stream 30, in or out of the electronic equipment enclosure 44, dependent on flow configuration. The internal baffling, and more particularly the flow guides 74, may include separate structural components or formed integral with the outer enclosure 48. In addition, the outer enclosure 48 may serve as an EMI filter. Further, in an embodiment a dehumidification system 76, as best illustrated in FIG. 6, may be included for controlling the air quality circulating within the outer enclosure 48 and the electronic enclosure 42 and disposed within the outer enclosure 48.

The disclosed thermal management system is modular in nature and may be configured to include separate thermal modules, such as thermal module 10, for each of the electronic component enclosures 42, or one common thermal module 10 for compactness. Furthermore, the thermal management system disclosed herein may employ a plurality of fan and motors, coupled to a single liquid-to-air heat exchanger, such as heat exchanger 16. The modularity of the thermal management system provides for the integration of varying types of electronic component with varying cooling and/or heating requirements into a single unit.

Accordingly, provided is a thermal management system, including a thermal module that combines a hydraulically-driven fan and a liquid-to-air heat exchanger into a stand-alone thermal management unit that can be placed anywhere one has access to a source of pressurized fluid. As a result, the thermal management system provides both air flow and heat transfer capability without requiring electricity to drive an electric fan. The thermal management system as disclosed provides placement anywhere where a source of cooled or heated air is required, but electricity may not be readily available or there is a need to eliminate any issues with electromagnetic interference.

Exemplary embodiments of the thermal module and implementation in a thermal management system are described in detail above. The thermal module is not limited to use with the specified MRI electronic component or coolant liquid stream as described herein, but rather, the thermal module can be utilized with any implementation where cooling and/or heating of electronic components is desired. Moreover, the present disclosure is not limited to the embodiments of the thermal management system described in detail above. Rather, other variations of the thermal management system may be utilized within the spirit and scope of the claims.

This written description uses examples to disclose the invention, including the best mode, and to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A thermal module comprising:
a hydraulic motor operable to rotate a motor output shaft;
a fan coupled to the motor output shaft;
at least one heat exchanger in fluidic communication with the fan to provide passage therethrough of an air stream in response to rotational movement of the fan; and
a conduit carrying a pressurized liquid stream through the hydraulic motor and each of the at least one heat exchanger,
wherein the pressurized liquid stream causes the motor output shaft to rotate, and
wherein heat in one of the air stream or the pressurized liquid stream is passed through each of the at least one heat exchanger and rejected into the other of the air stream or the pressurized liquid stream.

2. The thermal module as claimed in claim 1, wherein the fan is one of a puller-type fan or pusher-type fan.

3. The thermal module as claimed in claim 1, wherein the at least one heat exchanger is a cross-flow heat exchanger.

4. The thermal module as claimed in claim 1, wherein the at least one heat exchanger is a liquid-to-air heat exchanger.

5. The thermal module as claimed in claim 1, wherein the pressurized liquid stream is input at an inlet of the motor as a first temperature liquid stream and output from each of the at least one heat exchanger as a second temperature liquid stream, wherein the first temperature liquid stream has a temperature less than a temperature of the second temperature liquid stream and wherein the air stream is input into each of the at least one heat exchanger as a first temperature air stream and output from each of the at least one heat exchanger as a second temperature air stream, wherein a temperature of the first temperature air stream is greater than a temperature of the second temperature air stream.

6. The thermal module as claimed in claim 1, wherein the pressurized liquid stream is input into an inlet of the motor as a first temperature liquid stream and output from each of the at least one heat exchanger as a second temperature liquid stream, wherein a temperature of the first temperature liquid stream is greater than a temperature of the second temperature liquid stream and wherein the air stream is input into each of the at least one heat exchanger as a first temperature air stream and output from each of the at least one heat exchanger as a second temperature air stream, wherein a temperature of the first temperature air stream is less than a temperature of the second temperature air stream.

7. A thermal management system comprising:
an outer enclosure;

an electronic component enclosure disposed in the outer enclosure;
one or more electronic components disposed in the electronic component enclosure; and
at least one thermal module disposed in the outer enclosure and in fluidic communication with the one or more electronic components, the thermal module comprising:
  a hydraulic motor operable to rotate a motor output shaft;
  a fan coupled to the motor output shaft;
  at least one heat exchanger in fluidic communication with the fan to provide passage therethrough of an air stream in response to rotational movement of the fan; and
  a conduit carrying a pressurized liquid stream through the hydraulic motor and each of the at least one heat exchanger,
  wherein the pressurized liquid stream causes the motor output shaft to rotate, and
  wherein one of heat in the air stream passing through each of the at least one heat exchanger is rejected into the pressurized liquid stream or heat in the pressurized liquid stream passing through the conduit is rejected into the air stream passing through each of the at least one heat exchanger.

8. The system as claimed in claim 7, wherein the electronic components comprise MRI components.

9. The system as claimed in claim 7, further comprising at least one duct to carry one of a cooled air stream or a heated air stream exiting each of the at least one heat exchanger into the electronic component enclosure.

10. The system as claimed in claim 7, wherein the at least one heat exchanger is a liquid-to-air heat exchanger.

11. The system as claimed in claim 7, wherein the thermal management system is a cooling system.

12. The system as claimed in claim 11, wherein the liquid stream is input into an inlet of the motor as a first temperature liquid stream and output from each of the at least one heat exchanger as a second temperature liquid stream, wherein a temperature of the first temperature liquid stream is less than a temperature of the second temperature liquid stream and wherein the air stream is input into each of the at least one heat exchanger as a first temperature air stream and output from each of the at least one heat exchanger as a second temperature air stream, wherein a temperature of the first temperature air stream is greater than a temperature of the second temperature air stream.

13. The system as claimed in claim 7, wherein the thermal management system is a heating system.

14. The system as claimed in claim 13, wherein the liquid stream is input into an inlet of the motor as a first temperature liquid stream and output from each of the at least one heat exchanger as a second temperature liquid stream, wherein a temperature of the first temperature liquid stream is greater than a temperature of the second temperature liquid stream and wherein the air stream is input into each of the at least one heat exchanger as a first temperature air stream and output from each of the at least one heat exchanger as a second temperature air stream, wherein a temperature of the first temperature air stream is less than a temperature of the second temperature air stream.

15. The system as claimed in claim 7, wherein the liquid stream is split with a portion input into an inlet of each of the electronic component enclosure and the motor as a first temperature liquid stream, wherein an intermediate temperature liquid stream is output from the electronic component enclosure and input into the inlet of the motor, and wherein a second temperature liquid stream is output from the motor, wherein a temperature of the first temperature liquid stream is less than a temperature of the second temperature liquid stream and wherein the air stream is input into each of the at least one heat exchanger as a first temperature air stream and output from each of the at least one heat exchanger as a second temperature air stream, wherein a temperature of the first temperature air stream is greater than a temperature of the second temperature air stream.

16. The system as claimed in claim 7, wherein the liquid stream is input into an inlet of the electronic component enclosure as a first temperature liquid stream, wherein an intermediate temperature liquid stream is output from the electronic component enclosure and input into the inlet of the motor, and wherein a second temperature liquid stream is output from the motor, wherein a temperature of the first temperature liquid stream is less than a temperature of the second temperature liquid stream and wherein the air stream is input into each of the at least one heat exchanger as a first temperature air stream and output from each of the at least one heat exchanger as a second temperature air stream, wherein a temperature of the first temperature air stream is greater than a temperature of the second temperature air stream.

17. The system as claimed in claim 7, further comprising at least one flow guide directing the air stream in or out of the electronic component enclosure.

18. The system as claimed in claim 7, further comprising a dehumidification system in fluid communication with the air stream to control the quality of the air stream.

19. The system as claimed in claim 7, further comprising a feedback controller to adjust at least one of a flow and a pressure of the liquid stream to maintain an internal temperature of the electronic component enclosure.

20. A thermal management system comprising:
an outer enclosure;
one or more electronic component enclosures disposed in the outer enclosure;
one or more electronic components disposed in the one or more electronic component enclosures; and
at least one thermal module disposed in each of the one or more electronic component enclosures and in fluidic communication with the one or more electronic components, the thermal module comprising:
  a hydraulic motor rotatably operable to rotate a motor output shaft;
  a fan coupled to the motor output shaft;
  at least one heat exchanger in fluidic communication with the fan to provide passage therethrough of an air stream in response to rotational movement of the fan; and
  a conduit carrying a pressurized liquid stream through the hydraulic motor and each of the at least one heat exchanger,
  wherein the pressurized liquid stream causes the motor output shaft to rotate, and
  wherein heat in the air stream passing through each of the at least one heat exchanger is rejected into the pressurized liquid stream.

21. The system as claimed in claim 20, wherein the one or more electronic components comprise MRI components.

22. The system as claimed in claim 20, further comprising a conduit carrying a portion of the pressurized liquid stream through the one or more electronic component enclosures, wherein heat in the one or more electronic component enclosures is rejected into the pressurized liquid stream.

\* \* \* \* \*